United States Patent [19]
Pierce

[11] Patent Number: 5,826,608
[45] Date of Patent: Oct. 27, 1998

[54] RETRACTABLE TUBING REEL AND METHOD OF USE THEREOF

[76] Inventor: Elton Joe Pierce, 5526 Yeager Ct., Indianapolis, Ind. 46237

[21] Appl. No.: 392,556

[22] Filed: Feb. 21, 1995

Related U.S. Application Data

[63] Continuation of Ser. No. 276,207, Jul. 18, 1994, Pat. No. 5,392,808.

[51] Int. Cl.⁶ .................................................. B65H 75/34
[52] U.S. Cl. .................. 137/15; 137/355.16; 137/355.23
[58] Field of Search ........................ 137/355.23, 355.16, 137/355.2, 355.17, 15

[56] References Cited

U.S. PATENT DOCUMENTS

| | | |
|---|---|---|
| 1,537,637 | 5/1925 | Jarvis . |
| 2,286,904 | 6/1942 | Ewald . |
| 2,401,809 | 6/1946 | Ziegler . |
| 2,533,432 | 12/1950 | Clark . |
| 2,707,467 | 5/1955 | Pelzer et al. . |
| 2,907,534 | 10/1959 | Benstein . |
| 3,612,094 | 10/1971 | Hare . |
| 3,854,017 | 12/1974 | Crim . |
| 3,871,373 | 3/1975 | Jackson ..................................... 128/193 |
| 4,010,913 | 3/1977 | Guerster et al. . |
| 4,151,648 | 5/1979 | Hirth . |
| 4,446,884 | 5/1984 | Radar, Jr. . |
| 4,487,218 | 12/1984 | Sifri ............................... 137/355.23 X |
| 4,543,982 | 10/1985 | Wolfe . |
| 4,578,042 | 3/1986 | Evert ........................................ 441/117 |
| 4,671,315 | 6/1987 | Gardner .............................. 137/355.12 |
| 4,719,991 | 1/1988 | Diehn et al. . |
| 5,236,143 | 8/1993 | Dragon . |
| 5,381,820 | 1/1995 | Chandler ............................. 137/355.23 |
| 5,392,808 | 2/1995 | Pierce . |

*Primary Examiner*—Kevin Lee
*Attorney, Agent, or Firm*—Royston Rayzor Vickery Novak & Druce

[57] ABSTRACT

The present invention includes a retracting tubing reel for use in the delivery of therapeutic gas and a method for replacing fluid flow conduit in a retracting tubing reel used in the delivery of therapeutic gas to a patient. The retracting tubing reel comprises a housing wherein the housing includes at least two casing members that when mated together form an encasement for at least a portion of the retracting tubing reel. The casing members are releasably couplable to each other so that when each is disengaged from the other an interior of the housing is exposed. An inlet flow conduit passing through the housing provides fluid communication between an exterior end of the inlet flow conduit located outside the housing and an interior end of the inlet flow conduit located inside the housing. A flexible flow conduit is retractable into a coiled orientation within the housing. The flexible flow conduit is releasably couplable to the interior end of the inlet flow conduit so that the flexible flow conduit is removable from the housing while in the coiled orientation thereby facilitating the replacement of the flow conduit with another similarly coiled flow conduit.

17 Claims, 3 Drawing Sheets

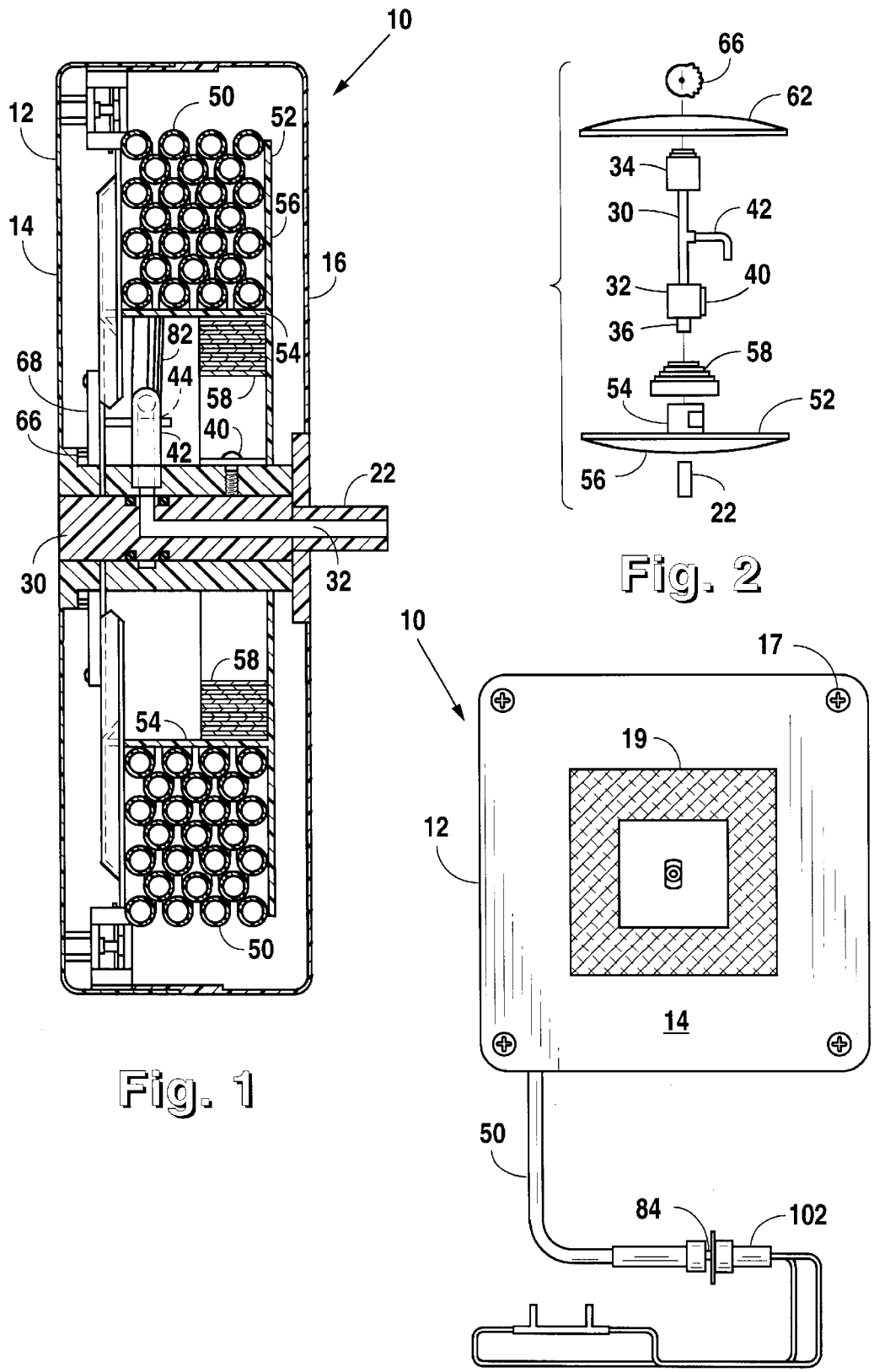

RETRACTABLE TUBING REEL AND METHOD OF USE THEREOF

This application is a continuation of Ser. No. 08/276,207 filed Jul. 18, 1994 now U.S. Pat. No. 5,392,808.

BACKGROUND OF THE INVENTION

1. Field of the Invention

The present invention relates generally to retractable tubing reels, and more particularly to a retractable tubing reel for supplying oxygen to a patient.

2. Description of the Related Art

Hospitalization sometimes requires that a patient receive oxygen therapy for the treatment of conditions resulting from oxygen deficiency. Oxygen therapy is used to combat acute arterial anoxia that may result from pneumonia, pulmonary edema, or obstruction to breathing. Oxygen therapy is also employed in congestive heart failure, coronary thrombosis, and following surgery. Oxygen therapy may be administered by nasal catheter, mask, funnel, oxygen tent, or special oxygen chamber, and usually in a concentration of seventy to one hundred percent. One of the most common methods of administering oxygen therapy is through nasal catheter to allow the patient the ability to move about normally and with less intrusions. The nasal catheter is connected to a stationary oxygen supply unit such as a tank, through tubing connected between the catheter and the stationary oxygen tank.

A patient undergoing oxygen therapy has limited movement due to the need to be close to a stationary oxygen supply unit. If a long tubing was connected between the stationary supply unit and the nasal catheter, the patient would have to worry about tangling and pinching of the tubing which would result in the oxygen being constricted and unavailable for the patient. Also, if excess tubing were to lay on a cold floor for any amount of time, condensation would commence in the tubing creating problems for the patient. What is needed is a means for allowing a patient undergoing oxygen therapy, or some other gas therapy, to freely move about a large area from a stationary gas supply unit. The oxygen, or gas, supplied to the patient must not be constricted or the flow to the patient reduced, and an indisposed patient must be able to use this means without exerting themselves. Some prior inventions have retraction mechanisms, however, these inventions are incompatible with oxygen therapy devices. Another problem associated with oxygen therapy is the necessity to easily service the tubing. The oxygen tubing must be removed for cleansing and sterilization on a regular maintenance schedule. Any device providing extra tubing must allow for facilitated servicing of that extra tubing, especially in a hospital where there might be hundreds of oxygen tubing that needs servicing.

Dragon, U.S. Pat. No. 5,236,143, discloses an intravenous tubing retractor apparatus including a container with a feed conduit, a retraction means with a spool, a pair of guide rollers, and a mounting boss with "L" shaped pivot arms.

Nederman, U.S. Pat. No. 4,224,960, discloses a wind-up device for flexible conduits comprising a drum in which a flexible conduit is enclosed, a stationary shaft, a coil spring assembly, a fixation element for effecting tensioning or release of the coil spring, the coil spring capable of rapid replacement without any need of releasing internal parts.

Guerster et al, U.S. Pat. No. 4,010,913, discloses a retriever reel for electrical or fluid lines comprising a stationary base, a drum, a continuous line, a spring, and a pair of clamps, the reel departing from the use of expensive slip rings or rotary joints.

SUMMARY OF THE INVENTION

The present invention is a device for allowing a patient undergoing oxygen therapy, or any other gas therapy, greater movement around a large area from a stationary oxygen supply unit. The patient is also relieved of the worry of tangling or pinching of their tubing because the excess tubing of the present invention can easily be retracted into a housing until further need arises for more tubing. The present invention also provides for facilitated servicing of the tubing without having to uncoil the tubing from the device.

The retractable tubing reel device of the present invention is utilized in conjunction with a stationary gas supply, such as a oxygen tank, and a patient intake unit such as a nasal catheter. The device consist of an attachable housing, an inlet flow conduit, a central swivel shaft, an extension unit, a flexible flow conduit, a gear assembly and a spring assembly.

The attachable housing, which encloses most of the other components of the device in a protective shell, has an attachment casing member and an inlet casing member which are essentially symmetrical in shape and mated to each other to form the-attachable housing. In the preferred embodiment, the attachable casing member is connected to the inlet casing member by four countersunk bolts which are easily removable for facilitated servicing of the device. The attachment casing member has a means for attachment to a base unit, the means for attachment in one embodiment being hook and loop connectors, commonly known as VELCRO. The inlet casing member has an inlet aperture in order to place the inlet flow conduit therethrough. The attachable housing has a conduit aperture for allowing ingress and egress of the flexible flow conduit. In the preferred embodiment, the attachable housing is composed of a resilient material, such as a hard plastic material, in order to protect the flexible flow conduit coiled in its interior.

The inlet flow conduit has an exterior end and an interior end and is a means for transferring oxygen, or some other gas, from a stationary gas supply to the device. In the preferred embodiment, the inlet flow conduit is a plastic tubing conducive to the transfer of oxygen. The exterior end of the inlet flow conduit is connected to the release valve of the stationary gas supply, and the interior end is placed therethrough the inlet aperture and connected to the central swivel shaft.

The central swivel shaft has a gear end and spring end, and is enclosed within the attachable housing. The central swivel shaft is essentially cylindrical in shape and is positioned at a horizontal axis across the attachable housing. The central swivel shaft has a central passageway for the flow of gas which is in flow communication with the inlet flow conduit and an extension passageway of the extension unit. The central swivel shaft act as a base for the other components of the device enclosed within the attachable housing.

The extension unit has a swivel end and a conduit end, and is connected perpendicular to the central swivel shaft, at its swivel end. The extension unit is connected to the middle of the central swivel shaft. The extension unit has an extension passageway therethrough which is in flow communication with the central passageway and the flexible flow conduit which is connected to the conduit end of the extension unit. The novel extension unit is capable of 180 degree movement in order to prevent tangling and miscoiling of the flexible flow conduit.

The flexible flow conduit has an inlet end and an outlet end, and is attached to the extension unit at its inlet end and through the conduit aperture of the attachable housing to a patient's gas intake unit at its outlet end. In the preferred embodiment, the flexible flow conduit is a plastic tubing conducive to transferring oxygen. The flexible flow conduit is wound around the spring reel during its coil state when there is no need for extension of the flexible flow conduit by the patient. When the patient departs from the stationary gas supply, the flexible flow conduit is extended from the attachable housing in order to provide the patient with the freedom to move about while still receiving gas from the stationary gas supply. When the patient moves toward the stationary gas supply, the flexible flow conduit is retracted by slightly tugging on it which recoils any excess flexible flow conduit. Recoiling of the flexible flow conduit prevents tangling and constriction of the conduit, and also prevents condensation build up in the conduit. During servicing of the flexible flow conduit, the inlet end is easily uncoupled from the extension unit, and the outlet end easily uncoupled from the patient gas intake unit. The coiled flexible flow conduit can then be removed for maintenance, and a new coiled flexible flow conduit installed in its place.

The gear assembly is enclosed within the attachable housing, and consists of a gear reel, gear catch lever, a half gear, and a gear compression spring. The gear reel is circular in shape and has a central aperture for engagement with the gear end of the central swivel shaft. The gear reel rotates reciprocally with the spring reel and forms a boundary for the flexible flow conduit. The gear catch lever is mounted to the gear reel and engages the half gear which is mounted to the gear end of the central swivel shaft. The gear compression spring is attached to the gear catch lever and assist in the engagement with the half gear. The half gear engages the gear catch lever during extension of the flexible flow conduit, and disengages the half gear during retraction of the flexible flow conduit.

The spring assembly is enclosed within the attachable housing and consists of a spring reel and a tension spring. The spring reel has a flat circular portion and a rim-like cylindrical portion perpendicular to the circular portion. The circular portion forms a second boundary for the flexible flow conduit opposite the boundary formed by the gear reel. The cylindrical portion is attached to the gear reel through a plurality of reel couplings. The spring reel has a central cavity in which the central swivel shaft is extended therethrough and engaged with the spring reel at the spring end of the central swivel shaft. The tension spring is connected to the central swivel shaft at a spring catch, both the tension spring and central swivel shaft enclosed by the cylindrical portion of the spring reel. The flexible flow conduit is wound around the perimeter of the cylindrical portion. The spring reel rotates in a first direction when the flexible flow conduit is extended, and in an opposite direction when the flexible flow conduit is retracted. The extension and retraction of the conduit controls the rotation of the spring reel and the gear reel around the stationary central shaft. In the preferred embodiment, the flexible flow conduit is approximately fifteen meters in length.

The present device is constructed to allow for facilitated maintenance of the tubing. The attachable casing member is attached to the inlet casing member by four countersunk bolts which allow for easy removal of the attachable casing member. Once the attachable casing member is removed, the flexible flow conduit can be uncoupled from the extension unit and removed from the housing without having to uncoil it. A new coiled flexible flow conduit can be installed and the attachable casing member reconnected to the inlet casing member, allowing for facilitated servicing of the device. This novel servicing feature of the present invention is beneficial in a hospital situation where tens, or even hundreds of tubing must undergo maintenance on a regular basis.

It is an object of the present invention to provide an improved retractable tubing reel.

It is a further object of the present invention to provide a device which retracts extraneous tubing.

It is a further object of the present invention to provide a device which allows a oxygen supply to be maintained in a separate room away from the patient.

It is a further object of the present invention to provide a device which reduces condensation in oxygen tubing.

It is a further object of the present invention to provide a device which allows for facilitated servicing of oxygen tubing.

BRIEF DESCRIPTION OF THE DRAWINGS

The present invention is further described in connection with the accompanying drawings, in which:

FIG. 1 is a drawing illustrating a side perspective view of the interior of the present invention.

FIG. 2 is a drawing illustrating an exploded view of the interior components of the present invention.

FIG. 3 is a drawing illustrating a side perspective view of the exterior of the present invention.

DETAILED DESCRIPTION OF THE INVENTION

Figure 4:
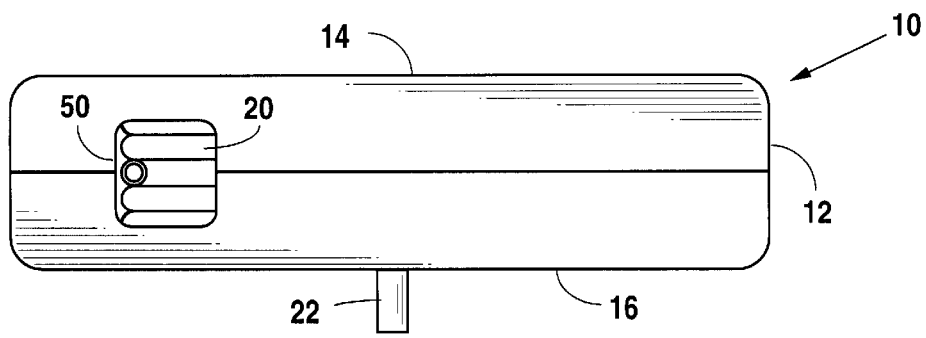
FIG. 4 is a drawing illustrating a bottom perspective view of the exterior of the present invention.

In FIG. 1, the device 10 has an attachable housing 12 consisting of an attachment casing member 14 and an inlet casing member 16. Casing members 14 and 16 are essentially symmetrical in shape and are mated to each other to form attachable housing 12. In the preferred embodiment, members 14 and 16 are connected to each other through a plurality of countersunk bolts 17. Removal of the plurality of countersunk bolts 17 allows for facilitated servicing of the device 10. In the preferred embodiment housing 12 is composed of a resilient material, such as a hard plastic material, to prevent damage to the other components of the device 10. In the preferred embodiment housing 12 forms a cylindrical protective shell around the other components of the device 10 which are enclosed within housing 10. Inlet casing member 16 has an inlet aperture for placement of an inlet flow conduit 22 therethrough. Inlet flow conduit 22 has an interior end and an exterior end, exterior end attached to and in flow communication with a stationary gas supply. Stationary gas supply can be a stationary oxygen supply tank, or a stationary supply tank for other medicinal gases. Inlet flow conduit 22 is coupled to the flow valve of stationary gas supply allowing for flow of the gas from supply to device 10. Interior end is attached a central swivel shaft 30 in the interior of housing 12. In the preferred embodiment, inlet flow conduit 22 is composed of a plastic tubing conducive to transferring of oxygen.

Central swivel shaft 30 is extended across a horizontal axis of housing 12, perpendicular to the faces of casing members 14 and 16. Central swivel shaft 30 is cylindrical shape, having a gear end 34 placed at the interior face of attachment casing member 14, and spring end 36 opposite gear end 34. Central swivel shaft 30 has a central passageway 32 extending from spring end 36 to a middle aperture 38. At spring end 36, inlet flow conduit 22 is coupled to shaft 30 allowing for flow communication between inlet flow conduit 22 and central passageway 32. Central swivel shaft 30 acts as a base for many of the other components of device 10 enclosed within housing 12. Shaft 30 is stationary about the horizontal axis of housing 12.

Extension unit s a swivel end 44 and conduit end, and is attached at its swivel end 44 to shaft 30 at middle aperture 38. Extension unit 42 is cylindrical having an extension passageway 48 therethrough, opened at both ends. Extension unit 42 is capable of rotating 180 degrees in order to prevent tangling and constriction of flexible flow conduit 50 while conduit 50 is within housing 12. Extension passage way 48 is in flow communication with central passageway 32 and flexible flow conduit 50 which is attached to extension unit 42 at conduit end. In this manner, gas from stationary gas supply is transferred from inlet flow conduit 22, to central passageway 32, to extension passageway 48, and to flexible flow conduit 50.

Flexible flow conduit 50 is an extended length tubing for allowing a patient to move about a large area away from stationary gas supply while safely and effectively transferring gas to the patient. In the preferred embodiment, conduit 50 ia a plastic tubing conducive to the transfer of oxygen. Conduit 50 is wound in a coil inside housing 12 during a coil state. During an extension state, conduit 50 is extended beyond housing 12 through conduit aperture 20. During a retraction state, conduit 50 is recoiled into housing 12. Conduit 50 has an inlet end 82 coupled extension unit 42 and an outlet end 84, coupled to a patient gas intake unit 102. During servicing, the coiled conduit 50 can be easily uncoupled from the extension unit 42 and the intake unit 102, and removed from housing 12 when casing member 14 is removed. A new coiled conduit 50 can be easily installed and casing member 14 reconnected. The ability to service the device without having to uncoil conduit 50 allows for substantial time saving on behalf of the service company.

Spring reel 52 consists of a cylindrical portion 54 and a flat circular portion 56. Conduit 5 is wound around cylindrical portion 54 of spring reel 52. Flat circular portion 56 of spring reel 52 forms an outer boundary for conduit 50, preventing tangling and constriction of conduit 50 while conduit 50 is wound around cylindrical portion 54. A gear reel 62 forms another outer boundary for conduit 50 opposite flat circular portion 56. Spring reel 52 and gear reel 62 are mounted on and rotate about shaft 30. Gear reel 62 rotates reciprocally with spring reel 52.

FIG. 2 is a drawing illustrating an exploded view of the interior components of the present invention. Referring to FIG. 2, central swivel shaft 30 has gear end 34 and spring end 36 with extension unit 42 perpendicular to shaft 30, attached above middle aperture 38. Tension spring 58 is placed around shaft 30 and attached at spring catch 40. Tension spring 58 is also attached to spring reel 52. Tension spring 58 tightens during the extension state of conduit 50 building up potential energy to be transformed into kinetic energy to recoil conduit 50 during the retraction state. Spring reel 52 is mounted on shaft 30 at spring end 36, cylindrical portion 54 encircling most of shaft 30. Inlet flow conduit 22 is attached at spring end 36 allowing for flow communication between conduit 22 and central passageway 32. On the opposite end of shaft 30, gear reel 62 is mounted on shaft 30 at gear end 34, and connected to spring reel 52 by a plurality of couplings. Half gear 66 is also mounted on shaft 30 at gear end 34.

There is illustrated in FIG. 3 a side perspective view of the exterior of the present invention. Referring to FIG. 3, attachment casing member 14 of housing 12 has conduit aperture 20, for allowing extension of flexible flow conduit 50 therethrough. Attachment casing member 14 has attachment means 19 on its exterior face. In the preferred embodiment, attachment means 19 is straps of hook and loop connectors, commonly known as VELCRO, adhesively attached to the exterior face of attachment casing member 14. Plurality of countersunk bolts 17 are placed therethrough casing member 14 and coupled to inlet casing member 16. In the preferred embodiment, plurality of countersunk bolts 17 are located at the corners of casing member 14 to provide for thorough connection of casing members 14 and 16. Conduit 50 is coupled at outlet end 84 to a patients gas intake unit 102, which in the preferred embodiment is a nasal oxygen catheter. However, intake unit 102 may be a oxygen mask, funnel or the like for delivering gas to the patient.

There is illustrated in FIG. 4 a bottom perspective view of the exterior of the present invention. Referring to FIG. 4, attachable housing 12 has conduit aperture 20 for allowing extension of flexible flow conduit 50. Conduit 50 is extended through aperture 20 during the extension state. Conduit 50 is uncoiled as the patient moves around a large area away from stationary gas supply and device 10. When the patient moves toward device 10, the extraneous conduit 50 is recoiled into housing 12 through aperture 20. Attachable housing 12 consists of attachment casing member 14 and inlet casing member 16 which are mated to each other. Inlet flow conduit 22 enters housing 12 at inlet aperture.

Figure 5:
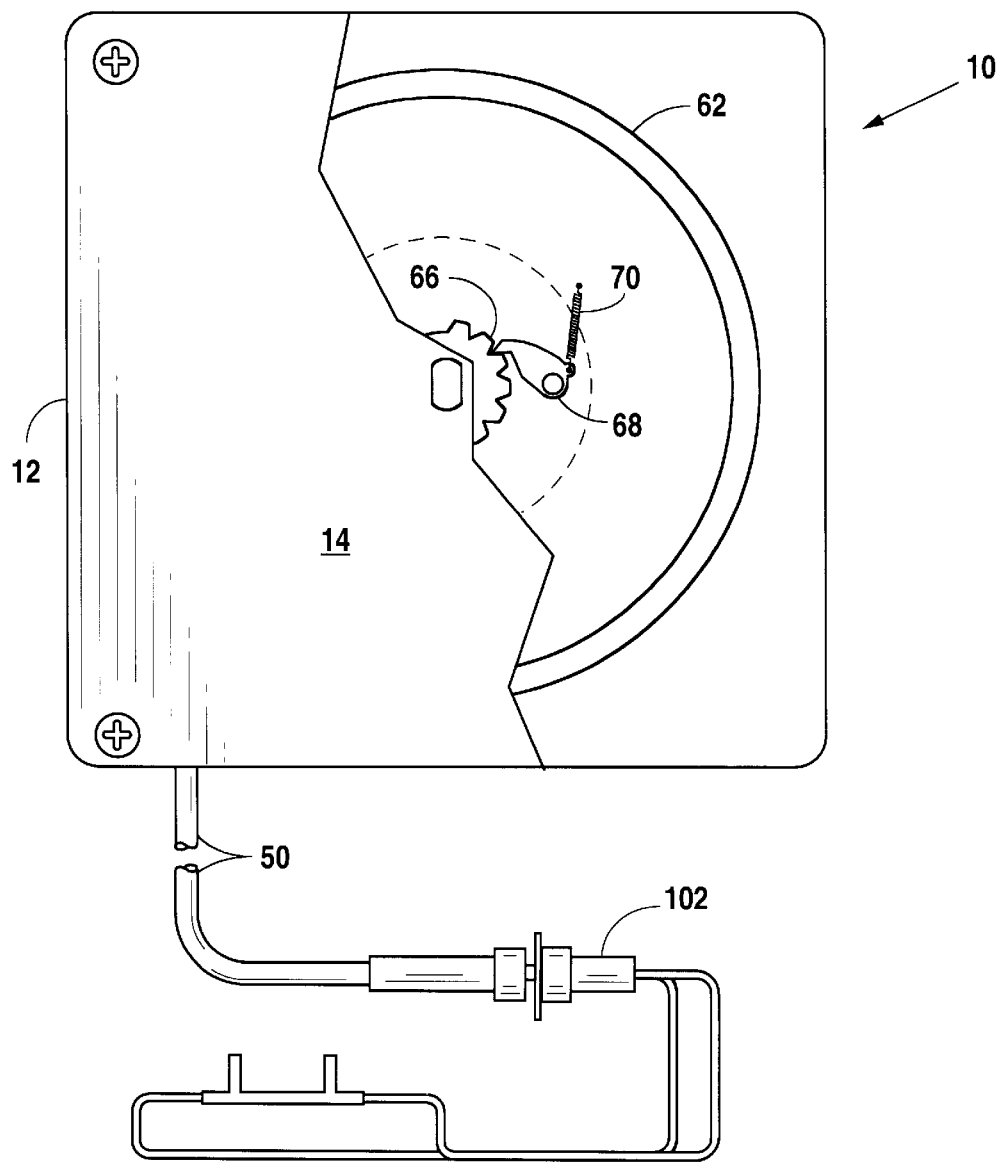
FIG. 5 is a drawing illustrating a side perspective view of the interior of the present invention.

There is illustrated in FIG. 5 a side perspective view of the interior of the present invention. Referring to FIG. 5, in the interior of housing 12 is gear reel 62 which acts as a boundary for flexible flow conduit 50. Gear catch lever 68 and gear compression spring 70 are attached to the exterior face of gear reel 62, on the opposite face from conduit 50. Spring 70 is attached to gear catch lever 68 which is engaged with half gear 66 which is mounted on central swivel shaft 30. During the extension state of conduit 50, lever 68 is engaged with half gear 66. During the retraction state of conduit 50, lever 68 is disengaged from gear 66. Conduit 50 is coupled at outlet end 84 to intake unit 102, allowing for flow communication between conduit 50 and intake unit 102. In the preferred embodiment, intake unit 102 is a nasal catheter which delivers oxygen to the patient through the patient's nostrils.

Figure 6:
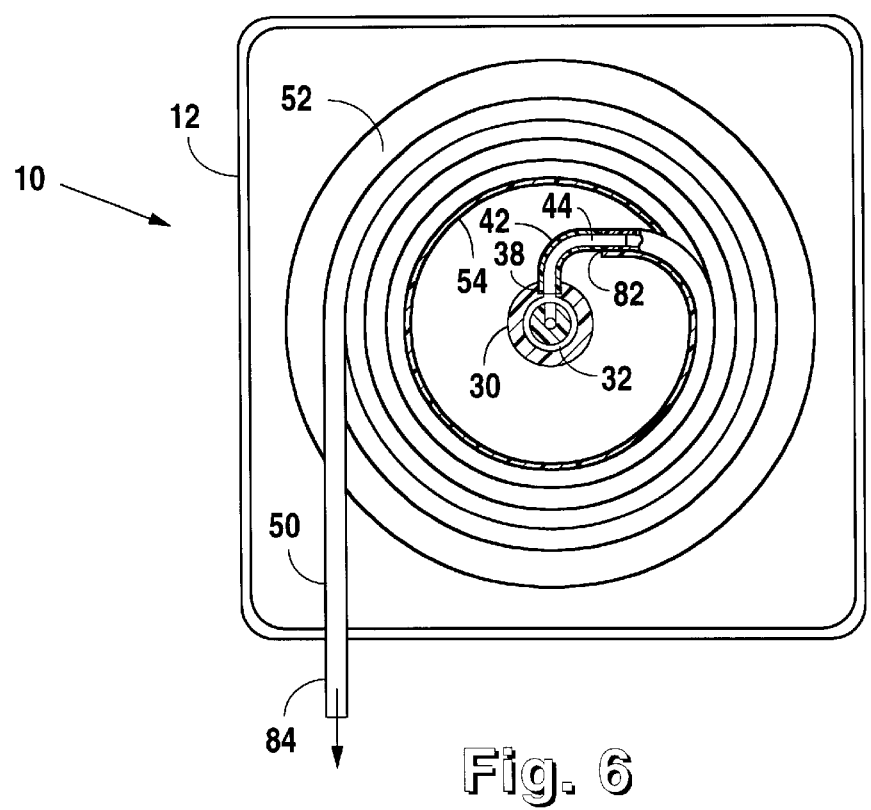
FIG. 6 is a drawing illustrating a side perspective view of the interior of the present invention.
Figure 7:
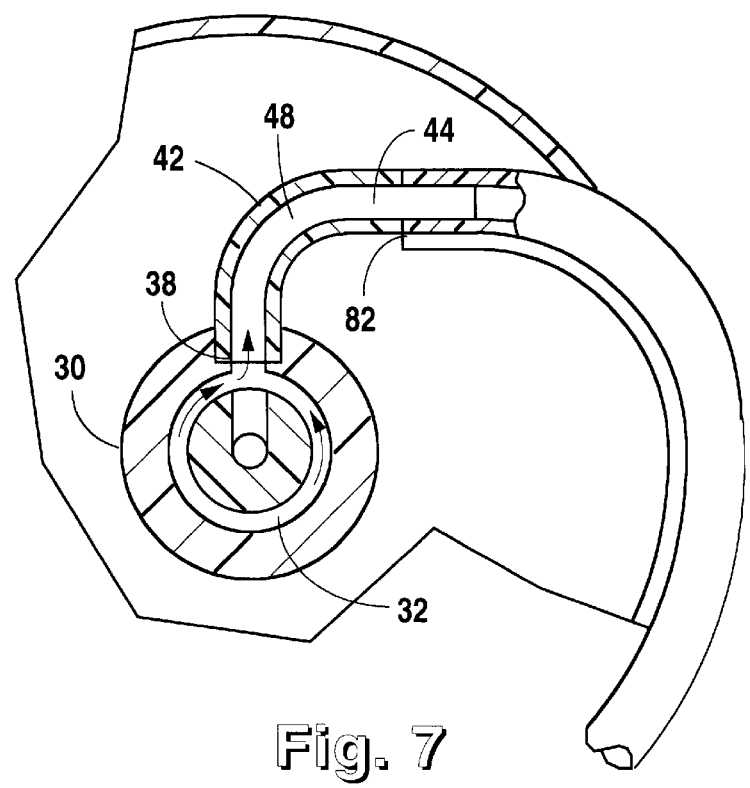
FIG. 7 is a drawing illustrating a side perspective view of the interior of the present invention.

There is illustrated in FIG. 6 a side perspective view of the interior of the present invention. There is illustrated in FIG. 7 a side perspective view of the interior of the present invention. Referring to FIGS. 6 and 7, flexible flow conduit 50 is wound in a coil around cylindrical portion 54 of spring reel 52. Inlet end 82 of conduit 50 is attached to extension unit 42 allowing for flow communication between extension passage way 44 and conduit 50. Extension unit 42 is attached to central swivel shaft 30 at middle aperture 38 allowing for flow communication between extension passageway 44 and central passageway 32. In this manner, gas, such as oxygen, is transferred from the central passageway 32 to extension passageway 44 to conduit 50. Conduit 50 is wound around cylindrical portion 54 in such a manner as to prevent tangling and constriction of conduit 50. Also, the one hundred eighty degree movement of extension unit 42 prevents tangling and constriction of conduit 50 during the retraction state. In the preferred embodiment, flexible flow conduit 50 is approximately fifteen meters in length, allowing the patient undergoing oxygen therapy to freely move about an approximately seven hundred square meter area. Device 10 may also be utilized in the deliver of nitrous oxide or other medicinal gases delivered to a patient.

Maintenance of tubing used in oxygen therapy, or other medicinal gas therapy, must be performed on a regular basis in order to prevent contamination of the tubing, which might prove fatal to a patient undergoing gas therapy. The tubing is removed from use in oxygen therapy, then cleansed and sterilized by a servicing company. The tubing is then returned for further use in oxygen therapy, or any other medicinal gas therapy. In a hospital where tens, or even hundreds of tubing must be serviced, the present invention allows for facilitated servicing of the tubing which results in significant time saving on behalf of the servicing company. During servicing, intake unit 102 is uncoupled from outlet end 84. Then, conduit 50 is recoiled into housing 12, and is in its coil state, wound around cylindrical portion 54 of spring reel 52. Casing member 14 is removed through unbolting plurality of countersunk bolts 17, which exposes the interior of housing 12. Gear reel 62 is uncoupled from spring reel 52 through plurality of couplings. Once gear reel 62 is removed from housing 12, conduit 50 is exposed and can be easily uncoupled from extension unit 42 at inlet end 82. Conduit 50 is then removed from housing 12, in its coiled state. A new conduit 50 in its coiled state is placed into housing 12 around cylindrical portion 54 and coupled to extension unit 42 at conduit's 50 inlet end 82. Gear reel 62 is then recoupled to spring reel 52 through plurality of couplings. Casing member 14 is then reconnected to casing member 16 through plurality of countersunk bolts 17. If inlet conduit 22 also needs servicing, then conduit 22 can be uncoupled from shaft 30 and gas supply, and a new conduit 22 installed. The intake unit 102 is then recoupled at outlet end 84 of conduit 50 and the device 10 is again ready for use in oxygen therapy, or any other form of medicinal gas therapy.

In operation, a patient undergoing oxygen therapy, or any other medicinal gas therapy, is in virtually constant need of oxygen. Prior to the present invention, the patient needed to be in close proximity to the stationary gas supply which limited their movement. Utilizing the present invention, inlet conduit 22 is coupled at exterior end to a releasing valve of stationary gas supply. Inlet conduit 22 is then placed therethrough inlet aperture and coupled to spring end 36 of central swivel shaft 30 at its interior end. Housing 12 is attached to stationary gas supply or some other stationary object through attachment means 19. Patient gas intake unit 102 is coupled to outlet end 84 of conduit 50. In the preferred embodiment, intake unit 102 is a nasal catheter which is placed about the patient's head with the nasal tubing insert into the patient's nostrils. An alligator clip may be used to attach conduit 50 to a patient's robe in order to prevent uncoupling of intake unit 102 and conduit 50 due to movement by the patient. Oxygen, or any other medicinal gas, is transferred from supply gas unit, through inlet flow conduit 22, through central passageway 32, through extension passageway 44, through flexible flow conduit 50, to intake unit 102 and to the patient. As the patient moves about their hospital room and beyond, conduit 50 is extended from housing 12. During the extension state, spring reel 52 and gear reel 62 are rotating about shaft 30 in a first direction. Also during the extension state, tension spring 58 is being tightened around central shaft 30, and gear catch lever 68 is engaged with half gear 66. If the patient moves toward device 10, or if there is excess conduit about the floor of the patient's room, the patient only need slightly tug conduit 50 which retracts any excess conduit 50 into housing 12. During the retraction state, tension spring 58 is slowly released, and gear catch lever 68 is disengaged from half gear 66. In this manner, the present invention allows for greater movement on behalf of the patient, and easy retraction of any excess tubing preventing tangling and constriction of the tubing, and also preventing condensation of the tubing.

While the preferred embodiment of the invention has been shown and described, it will be apparent to those skilled in this art that various modifications may be made in the embodiment without departing from the spirit of the present invention. Therefore, the embodiments of the invention in which an exclusive property or privilege is claimed are defined as follows:

1. A retracting tubing reel for use in the delivery of therapeutic gas to a patient, said retracting tubing reel comprising:

a housing wherein said housing includes at least two casing members that when mated together form an encasement for at least a portion of said retracting tubing reel;

said casing members being releasably couplable to each other so that when each is disengaged from the other an interior of said housing is exposed;

an inlet flow conduit passing through said housing for providing fluid communication between an exterior end of said inlet flow conduit located outside said housing and an interior end of said inlet flow conduit located inside said housing;

a flexible flow conduit for providing the delivery of therapeutic gas therethrough;

said flexible flow conduit being retractable into a coiled orientation within said housing; and said flexible flow conduit being releasably couplable to said interior end of said inlet flow conduit so that said flexible flow conduit is removable from said housing while in the coiled orientation thereby facilitating the replacement of said flow conduit with another similarly coiled flow conduit.

2. The retracting tubing reel for use in the delivery of therapeutic gas to a patient as recited in claim 1 wherein said coiled orientation of said flexible flow conduit comprises a plurality of flexible flow conduit windings.

3. The retracting tubing reel for use in the delivery of therapeutic gas to a patient as recited in claim 1, said retracting tubing reel further comprising:

a central swivel shaft oriented across said housing for rotation therein; and a spring assembly coupled to said swivel shaft for applying a tension force on said flow conduit during retraction.

4. The retracting tubing reel for use in the delivery of therapeutic gas to a patient as recited in claim 3, said central swivel shaft further comprising a gear end and a spring end opposite said gear end wherein each end is coupled to said housing for maintaining said swivel shaft in a horizontal relationship thereto.

5. The retracting tubing reel for use in the delivery of therapeutic gas to a patient as recited in claim 3, said retracting tubing reel further comprising:

a gear assembly coupled to said swivel shaft for controlling rotation of said swivel shaft during extension and retraction of said flow conduit; and said gear assembly providing a boundary for retaining said coiled flow conduit upon said swivel shaft.

6. The retracting tubing reel for use in the delivery of therapeutic gas to a patient as recited in claim 3, said retracting tubing reel further comprising:

a spring assembly coupled to said swivel shaft for controlling rotation of said swivel shaft during extension and retraction of said flow conduit; and said spring assembly providing a boundary for retaining said coiled flow conduit upon said swivel shaft.

7. The retracting tubing reel for use in the delivery of therapeutic gas to a patient as recited in claim 3, said retracting tubing reel further comprising:

a gear assembly coupled to said swivel shaft for controlling the direction of rotation of said swivel shaft during extension and retraction of said flow conduit, wherein said gear assembly provides a first boundary for retaining said coiled flow conduit upon said swivel shaft; and a spring assembly coupled to said swivel shaft for applying a tension force to said swivel shaft during extension and retraction of said flow conduit, wherein said spring assembly provides a second boundary for retaining said coiled flow conduit upon said swivel shaft opposite said first boundary of said gear assembly.

8. The retracting tubing reel for use in the delivery of therapeutic gas to a patient as recited in claim 1 wherein said retracting tubing reel is fluidly connected between a therapeutic gas source and a patient nasal catheter.

9. The retracting tubing reel for use in the delivery of therapeutic gas to a patient as recited in claim 1 wherein said retracting tubing reel further comprises a connection means at an exterior surface of said housing for anchoring said retracting tubing reel.

10. The retracting tubing reel for use in the delivery of therapeutic gas to a patient as recited in claim 9 wherein said connection means comprises hook and loop connectors.

11. A method for replacing fluid flow conduit in a retracting tubing reel used in the delivery of therapeutic gas to a patient, said method comprising the steps of:

providing a retracting tubing reel, wherein said tubing reel comprises:
a housing having at least two casing members that when mated together form an encasement for at least a portion of said retracting tubing reel;
said casing members being releasably couplable to each other so that when each is disengaged from the other an interior of said housing is exposed;
a flexible flow conduit for providing delivery of therapeutic gas therethrough;
said flexible flow conduit being retractable into a coiled orientation within said housing and being releasably couplable to said housing;

retracting said flow conduit into said housing thereby forming a flow conduit coil within said housing;

disengaging said flow conduit from said housing; and removing said flow conduit coil from said retracting tubing reel while in the coiled orientation.

12. The method for replacing fluid flow conduit in a retracting tubing reel used in the delivery of therapeutic gas to a patient as recited in claim 11 wherein the step of providing a retracting tubing reel further comprises said coiled orientation of said flexible flow conduit having a plurality of flexible flow conduit windings.

13. The method for replacing fluid flow conduit in a retracting tubing reel used in the delivery of therapeutic gas to a patient as recited in claim 11, said method further comprising the steps of:

installing a second flow conduit coil within said tubing reel; and connecting said second flow conduit to said retracting tubing reel for fluid communication therewith.

14. The method for replacing fluid flow conduit in a retracting tubing reel used in the delivery of therapeutic gas to a patient as recited in claim 13, said method further comprising the steps of connecting said retracting tubing reel in fluid communication between a therapeutic gas source and a patient nasal catheter.

15. A retracting tubing reel for use in the delivery of therapeutic gas to a patient, said retracting tubing reel comprising:

a central swivel shaft having a central passageway therethrough for delivery of therapeutic gas;

a flexible flow conduit being in fluid communication with said central passageway;

a substantially cylindrical portion for providing support for said flexible flow conduit;

said flexible flow conduit being retractable into a coiled orientation about said substantially cylindrical portion;

a housing wherein said housing includes at least one casing member; and an inlet flow conduit passing through said housing for providing fluid communication between an exterior end of said inlet flow conduit located outside said housing and an interior end of said inlet flow conduit located inside said housing, said flexible flow conduit being releasably couplable to said interior end of said inlet flow conduit so that said flexible flow conduit is removable from said housing while in the coiled orientation thereby facilitating the replacement of said flow conduit with another similarly coiled flow conduit.

16. The retracting tubing reel for use in the delivery of therapeutic gas to a patient as recited in claim 15 wherein said coiled orientation of said flexible flow conduit comprises a plurality of flexible flow conduit windings.

17. The retracting tubing reel for use in the delivery of therapeutic gas to a patient as recited in claim 15, further comprising:

a spring assembly coupled to said swivel shaft for applying a tension force on said flow conduit during retraction.

* * * * *